US011622735B1

(12) United States Patent
Ghazi et al.

(10) Patent No.: US 11,622,735 B1
(45) Date of Patent: *Apr. 11, 2023

(54) PLURAL-PLANE NARROW-BEAM COMPUTED TOMOGRAPHY

(71) Applicant: MALCOVA, Inc., Newark, CA (US)

(72) Inventors: Peymon Mirsaeid Ghazi, Fremont, CA (US); Tara Reneé Ghazi, Fremont, CA (US)

(73) Assignee: MALCOVA, INC., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/970,158

(22) Filed: Oct. 20, 2022

(51) Int. Cl.
A61B 6/03 (2006.01)
A61B 6/00 (2006.01)

(52) U.S. Cl.
CPC ............ A61B 6/03 (2013.01); A61B 6/482 (2013.01); A61B 6/4241 (2013.01)

(58) Field of Classification Search
CPC .......... A61B 6/03; A61B 6/482; A61B 6/4241
See application file for complete search history.

(56) References Cited

U.S. PATENT DOCUMENTS

| 4,145,610 A | 3/1979 | Perilhou |
| 4,190,773 A | 2/1980 | Braden et al. |
| 4,196,352 A | 4/1980 | Berninger et al. |
| 4,315,146 A | 2/1982 | Rudin |
| 4,403,338 A | 9/1983 | Rudin et al. |
| 4,975,933 A | 12/1990 | Hampel |
| 5,966,422 A | 10/1999 | Dafni et al. |
| 6,438,210 B1 | 8/2002 | Castleberry |
| 6,744,852 B2 | 6/2004 | Klotz et al. |
| 6,990,171 B2 | 1/2006 | Toth et al. |
| 7,088,799 B2 | 8/2006 | Hoffman |
| 8,199,883 B2 | 6/2012 | Arenson et al. |
| 8,325,879 B2 | 12/2012 | Loos et al. |
| 9,208,918 B2 | 12/2015 | Tybinkowski et al. |
| 9,392,984 B2 | 7/2016 | Pelc et al. |
| 10,531,844 B1 | 1/2020 | Ghazi et al. |
| 10,799,193 B2* | 10/2020 | Ghazi ...................... A61B 6/06 |
| 2004/0013225 A1 | 1/2004 | Gregerson et al. |
| 2005/0013411 A1 | 1/2005 | Yahata et al. |
| 2009/0080604 A1 | 3/2009 | Shores et al. |
| 2011/0013742 A1 | 1/2011 | Zaiki et al. |
| 2013/0235973 A1 | 9/2013 | Murakoshi et al. |
| 2014/0098930 A1* | 4/2014 | Litzenberger .......... A61B 6/025 378/4 |

(Continued)

FOREIGN PATENT DOCUMENTS

| JP | H0638957 A | 2/1994 |
| JP | H09149898 A | 6/1997 |

(Continued)

OTHER PUBLICATIONS

Ghazi et al.: A fluence modulation and scatter shielding apparatus for dedicated breast CT: Theory of operation. Med Phys. 47(4):1590-1608 doi:10.1002/mp.14026 (2020).

(Continued)

Primary Examiner — Courtney D Thomas
(74) Attorney, Agent, or Firm — Wilson Sonsini Goodrich & Rosati

(57) ABSTRACT

Described herein are systems and methods for performing plural-plane narrow-beam computed tomography.

30 Claims, 21 Drawing Sheets

(56) References Cited

U.S. PATENT DOCUMENTS

| | | |
|---|---|---|
| 2015/0279496 A1 | 10/2015 | Bauer |
| 2015/0366522 A1 | 12/2015 | Besson |
| 2016/0035450 A1 | 2/2016 | Date et al. |
| 2016/0081636 A1 | 3/2016 | Kremer et al. |
| 2016/0361036 A1 | 12/2016 | Ray et al. |
| 2018/0289348 A1 | 10/2018 | Cox et al. |
| 2018/0317867 A1 | 11/2018 | Boone et al. |

FOREIGN PATENT DOCUMENTS

| | | |
|---|---|---|
| JP | 2019010443 A | 1/2019 |
| WO | WO-2014058775 A1 | 4/2014 |
| WO | WO-2016126829 A1 | 8/2016 |
| WO | WO-2017073996 A1 | 5/2017 |
| WO | WO-2018165285 A1 | 9/2018 |
| WO | WO-2020167840 A1 | 8/2020 |
| WO | WO-2021030192 A1 | 2/2021 |

OTHER PUBLICATIONS

Ghazi: Reduction of scatter in breast CT yields improved microcalcification visibility. Phys Med Biol. 65(23):235047:1-21 doi:10.1088/1361-6560/abae07 (2020).

PCT/US2020/017760 International Search Report and Written Opinion dated May 4, 2020.

PCT/US2020/045415 International Search Report and Written Opinion dated Sep. 9, 2020.

U.S. Appl. No. 16/557,321 Office Action dated Jan. 3, 2020.

U.S. Appl. No. 16/557,321 Office Action dated May 28, 2020.

\* cited by examiner

US 11,622,735 B1

PLURAL-PLANE NARROW-BEAM COMPUTED TOMOGRAPHY

GOVERNMENT FUNDING

This invention was made with government support under Grant Number 1R43CA261381-01 awarded by the United States department of Health and Human Services (HSS), National Institutes of Health (NIH), National Cancer Institute (NCI). The government has certain rights in the invention.

BACKGROUND

Computed Tomography (CT) is a modality of imaging the internal areas of an object using x-ray equipment, special image acquisition techniques, and image reconstruction methods.

TECHNICAL FIELD

The present subject matter relates to an apparatus and methods for x-ray computed tomography of an object.

SUMMARY

In diagnostic x-ray CT, the dominant photon interaction type is Compton scattering (also known as incoherent scattering). In a Compton scattering event, an x-ray photon transitioning through an object interacts with an electron of an atom. During the interaction, a part of the energy of the photon is transferred to the electron. After the interaction, the reduced-energy x-ray photon continues its transition through the object on a different path than the path it was on prior to the scatter event. Due to the stochastic nature of the scatter events, it is impossible to deterministically specify the exact location of the scatter event. These scatter events, being indeterminate, are a form of undesirable contamination when received at the detector. Ideally, to maximize determinate signal at the detector, acquired projections would be free of scattered x-rays. In practice though, projections contain "primary" photons, as well as scattered photons. Primary photons are defined as the acquired photons that transition through the object without undergoing any scatter event.

Acquiring x-ray scatter in x-ray detector leads to reduced image quality throughout the frequency response of the imaging system. Some unwanted effects, such as shading artifacts, can be mitigated to a certain extent after a scan is complete. Some unwanted effects or artifacts, though, are practically impossible to correct retroactively—for example the deterioration of contrast resolution of small deposits of calcium (also known as microcalcifications) in a cancer diagnostic CT scan.

The ideal solution to problems that stem from acquiring scatter photons is to simply prevent the scattered photons from being acquired. A machine to accomplish this is described in U.S. Pat. No. 10,799,193 and a publication (Ghazi P. Phys. Med. Biol., 65(23), 235047). These disclosures describe a CT image acquisition apparatus, and technique of operating the apparatus, that result in near scatter-free projections. This apparatus, and the associated method of imaging, is referred to hereinafter as "Flat-Plane Narrow-Beam CT."

FIGS. 1A-1C illustrate the Flat-Plane Narrow-Beam CT image acquisition apparatus and methodology. FIG. 1A shows a side view of this setup. At its core, a Flat-Plane Narrow-Beam CT system is comprised of a CT scanner 101 where an object 102 is measured using an x-ray beam 103 that is generated at an x-ray unit 104 and captured at a detector unit 105. In this setup, the cone-angle 106 of the CT system is defined as the angular coverage of the beam interacting with the object and parameterized as α.

As shown in FIG. 1B, in Flat-Plane Narrow-Beam CT, the sourced beam in the x-ray source 104 is substantially collimated by an x-ray collimator 107. The collimator 107 travels with the x-ray source 104 around the object 102 such that the sourced beam is always collimated. The collimation is such that only a narrow vertical beam can exit the collimator through a slot 108. The resulting beam is hereinafter referred to as a "narrow beam." The specificities of the narrow beam's shape are dependent on the shape of the collimator slot 108, and its distance from the x-ray source 104. The details of the collimator slot, and its impact on the shape of the narrow beam, are disclosed in a publication (Ghazi P., Med Phys, 47(4), 1590-1608).

After interacting with the object 102, the primary photons of the narrow beam are captured in the detector unit 105. The detection unit has a substantially elongated sensitive area, large enough to capture the entirety of the primary photons within the narrow beam. This implies that at any instance of time during an x-ray exposure, only a limited part—and not all—of the object 102 is being measured. In order to measure the entire structure of the object in Flat-Plane Narrow-Beam CT, the detector physically rotates around the object along a circular trajectory 109. The narrow beam that is formed in the collimator 107 is incident on the detector 105. Therefore, similar to the detector unit 105, the collimator 107 physically rotates circularly 110. The circular motions of these two units are controlled in a control unit such the narrow beam sweeps the entire object. In CT, tomographic imaging implies that the object 102 is measured from different view angles. Therefore, as shown in FIG. 1B, in Flat-Plane Narrow-Beam CT, the source moves along a flat path 111 around the object from a starting point 112 to a finish point 113.

FIG. 1C provides a planar view of the Flat-Plane Narrow-Beam CT image acquisition geometry. As illustrated, at any instance of time during an x-ray exposure in Flat-Plane Narrow-Beam CT, a narrow beam 103 with an angular coverage of β 114 measures a fraction of the object 102. In each view angle, the measurement continues until the narrow beam traces the entire angular coverage of the object. In FIG. 1C, the entire angular coverage of the object is hereinafter referred to as the "fan angle" and parameterized as γ 115. Note that in Flat-Plane Narrow-Beam CT, the angular coverage of the narrow beam (parameter β) is substantially less that the fan angle coverage of the x-ray source (parameter γ). Therefore, at each view angle of the x-ray source, it is necessary for the detector 105 to rotate around the object 102 to measure it completely. As stated previously, x-ray source physically rotates around the object along a path 111. In Flat-Plane Narrow-Beam CT, if the objective is to generate isotropic voxels in the resulting CT image, then the angular coverage of the x-ray source must be at least 180 degrees plus the fan angle. Concretely, the trajectory of the source must be selected such that $$\gamma < \theta \qquad \text{Equation 1.}$$

A primary advantage of Flat-Plane Narrow-Beam CT is the significant reduction in acquisition of scattered x-rays in the projections that results compared to other CT methods. For instance, the results of a study disclosed in a publication (Ghazi P. Phys. Med. Biol., 65(23), 235047) reveal that the scatter portion of the total acquired data can be reduced from over 50% in cone-beam CT to less than 10% in Flat-Plane Narrow-Beam CT. Building upon this advantage, then, would be a design that makes possible the imaging of not just simple-shaped objects, but those with complex shapes as well. A case example distinguishing between image acquisition of a simple versus a complex shape is shown in FIG. 2 which depicts a cross-sectional view of a patient breast being imaged on a Flat-Plan Narrow-Beam CT device. FIG. 2 assumes a similar geometry to that shown in FIG. 1B. In FIG. 2 a patient 209 is positioned such that they are laying prone, or face-down, on a Flat-Plane Narrow-Beam CT system designed specifically for imaging the breast anatomy. The object of interest in this case is the entire breast region 211, a complex shape comprised of breast region 212 and breast region 213. In this setup, an x-ray source (not depicted) rotates around the breast 211 following a flat-plane trajectory 210, depicted here from a side view as a straight line. As shown, the entire body of the patient 209 is above line 210, and only breast region 213 lies within the field-of-view created by the x-ray source. The breast region 211 is subdivided by plane 210 into its lower (anterior) region 213, which is captured by a simplified half prolate ellipsoid model and can be successfully imaged with Flat-Plane Narrow-Beam CT, and an upper (posterior) region 212 which is not captured by a simplified model and is not accessible for imaging.

As shown, this image acquisition geometry renders part 212 of the breast anatomy, which in a human is described as the posterior breast region nearest the chest wall and axilla region in the underarm area, outside the field of view of the imaging system. The anterior region 213 of the breast, however, is able to be fully measured. In applications such as breast imaging for cancer detection, usage of the Flat-Plane Narrow-Beam CT geometry as depicted would only deliver information regarding the existence or development of cancer in an area 213 of the breast tissue, but not in other areas 212. The realistic model of the breast, 211, which includes both posterior 212 and anterior 213 regions is an example of a complex or irregularly-shaped object that cannot be imaged in its entirety with a Flat-Plane Narrow-Beam CT system. This is due to the mechanical restriction of the movement pathway of the x-ray source to that of a flat, 2-dimensional plane (see the source trajectory 111 in FIG. 1B).

It is an objective of the present disclosure to introduce a CT image acquisition apparatus and method of imaging that builds upon the advantages of Flat-Plane Narrow-Beam CT, yielding images uncontaminated by artifacts resulting from scattered radiation, and allows for total measurement of objects possessing complex or irregular shapes (such as the entire breast 211 as shown in FIG. 2), without introducing unwanted exposure of adjacent areas of the anatomy or other objects which are not the subject of interest to radiation dose. In the disclosed subject matter this significant enhancement to Flat-Plane Narrow-Beam CT is achieved via utilization of an x-ray source trajectory or pathway that allows for the focal imaging of a complex object of interest in its entirety. The image acquisition apparatus and methodology of imaging of the present disclosure is hereinafter referred to as "Plural-Plane Narrow-Beam CT."

Accordingly, in one aspect, disclosed herein are plural-plane narrow-beam computed tomography (CT) systems comprising: an x-ray generation assembly affixed to a first rotational apparatus configured to rotate on a first trajectory at a first rotational speed, the x-ray generation assembly comprising at least one x-ray tube and a rotational collimator associated with each x-ray tube, the x-ray generation assembly configured to generate a narrow collimated narrow beam of x-ray photons having a fan angle of less than 5.8 degrees; an x-ray detection assembly affixed to a second rotational apparatus configured to rotate on a second trajectory at a second rotational speed, wherein the x-ray detection assembly is mechanically decoupled from the first rotational apparatus and comprises at least one line detector configured to detect the narrow beam of x-ray photons, wherein the line detectors of the x-ray detection assembly operate in time-delay-integration mode; and a controller configured to perform at least: controlling the first rotational apparatus to rotate the x-ray generation assembly on the first trajectory at the first rotational speed; controlling the second rotational apparatus to rotate the x-ray detection assembly on the second trajectory at the second rotational speed, around a target; and controlling the speed and phase of rotation of the rotational collimator and the speed and phase of rotation of the x-ray detection assembly such that primary x-ray photons within the narrow beam of x-ray photons become incident upon the at least one line detector; wherein the second rotational speed is at least 10 times higher than the first rotational speed, wherein the first trajectory and the second trajectory are non-coplanar, wherein the first trajectory comprises less than 360 degrees rotation, and wherein the secondary trajectory comprises more than 360 degrees rotation. In some embodiments, the first trajectory varies both positively and negatively upon an axis perpendicular to the cross-sectional two-dimensional plane of rotation of the first rotational robotic. The plural-plane narrow-beam CT system of claim 1, wherein the system does not comprise a gantry mechanically connecting the first rotational apparatus and the second rotational apparatus. In some embodiments, each line detector has a height at least an order of magnitude larger than its width. In some embodiments, the first rotational apparatus comprises a platform suspended from a vertically superior railing by which travel of x-ray generation assembly along the first trajectory is enacted. In some embodiments, the first rotational apparatus comprises a robotically controlled supporting platform by which travel of x-ray generation assembly along the first trajectory is enacted. In some embodiments, the second trajectory has a smaller average radius than the first trajectory. In some embodiments, the rotational collimator is configured to rotate about an axis of rotation on the first trajectory and perpendicular to the first trajectory. In some embodiments, the first trajectory comprises a non-linear ovoid plane. In various embodiments, the beam of x-ray photons incident on the x-ray detector comprises, in total, less than 20%, less than 15%, less than 10%, less than 5%, or less than 1% scattered photons. In some embodiments, the target is an anatomical target. In further embodiments, the anatomical target is a human extremity. In other embodiments, the anatomical target is a human breast. In yet other embodiments, the anatomical target is an entire human body.

In another aspect, disclosed herein are plural-plane narrow-beam computed tomography (CT) systems comprising: a first x-ray generation assembly affixed to a first rotational apparatus configured to rotate on a first trajectory at a first rotational speed; a second x-ray generation assembly affixed to a second rotational apparatus configured to rotate on a second trajectory at a second rotational speed; wherein each x-ray generation assembly comprises an x-ray tube and a rotational collimator, and wherein each x-ray generation assembly is configured to generate a narrow collimated beam of x-ray photons; an x-ray detection assembly affixed to a third rotational apparatus configured to rotate on a third trajectory at a third rotational speed, wherein the x-ray detection assembly is mechanically decoupled from the first and second rotational apparatuses and comprises at least one line detector configured to detect the narrow beams of x-ray photons; and a controller configured to perform at least: controlling the first rotational apparatus to rotate the first x-ray generation assembly on the first trajectory at the first rotational speed; controlling the second rotational apparatus to rotate the second x-ray generation assembly on the second trajectory at the second rotational speed; controlling the third rotational apparatus to rotate the x-ray detection assembly on the third trajectory at the third rotational speed, around a target; and controlling the speed and phase of rotation of the rotational collimator of the first and second x-ray generation assemblies and the speed and phase of rotation of the x-ray detection assembly such that primary x-ray photons of the narrow beams generated by the first and second x-ray generation assemblies become incident upon the at least one line detector; wherein the first trajectory comprises a rotation of at least 90 degrees plus one-half fan-angle, wherein the second trajectory comprises a rotation of at least 90 degrees plus one-half fan-angle, and wherein the third trajectory comprises more than 360 degrees rotation. In some embodiments, the first trajectory and the second trajectory are non-equivalent. In some embodiments, the first and second rotational apparatuses comprise independent platforms suspended from independent vertically superior railings. In some embodiments, the first and second rotational apparatuses are mounted upon independent robotic platforms. In some embodiments, the system does not comprise a gantry mechanically connecting the first rotational apparatus and the third rotational apparatus or the second rotational apparatus and the third rotational apparatus. In some embodiments, each line detector has a height at least an order of magnitude larger than its width. In some embodiments, the second trajectory has a smaller average radius than the first trajectory. In various embodiments, the beams of x-ray photons incident on the x-ray detector comprises, in total, less than 20%, less than 15%, less than 10%, less than 5%, or less than 1% scattered photons. In some embodiments, the target is an anatomical target. In further embodiments, the anatomical target is a human extremity. In other embodiments, the anatomical target is a human breast. In yet other embodiments, the anatomical target is an entire human body.

In yet another aspect, disclosed herein are methods of performing plural-plane narrow-beam computed tomography (CT) to image a target, the method comprising: generating, by an x-ray generation assembly, a collimated narrow beam of x-ray photons having a fan angle of less than 5.8 degrees, the x-ray generation assembly affixed to a first rotational apparatus configured to rotate on a first trajectory at a first rotational speed, the x-ray generation assembly comprising at least one x-ray tube and a rotational collimator associated with each x-ray tube; detecting, by an x-ray detection assembly, the narrow beam of x-ray photons, the x-ray detection assembly affixed to a second rotational apparatus configured to rotate on a second trajectory at a second rotational speed, wherein the x-ray detection assembly is mechanically decoupled from the first rotational apparatus and comprises at least one line detector, and wherein the at least one line detector operates in time-delay-integration mode; and performing, by a controller unit, operations comprising: controlling the first rotational apparatus to rotate the x-ray generation assembly on the first trajectory at the first rotational speed; controlling the second rotational apparatus to rotate the x-ray detection assembly on the second trajectory at the second rotational speed, around a target; and controlling the speed and phase of rotation of the rotational collimator and the speed and phase of rotation of the x-ray detection assembly such that primary x-ray photons within the narrow beam of x-ray photons become incident upon the at least one line detector; wherein the second rotational speed is at least 10 times higher than the first rotational speed, wherein the first trajectory and the second trajectory are non-coplanar, wherein the first trajectory comprises less than 360 degrees rotation, and wherein the secondary trajectory comprises more than 360 degrees rotation. In some embodiments, a charge hand-off speed of the time-delay-integration mode of the at least one line detector is equal to the tangential speed of the detection assembly as it rotates on the second trajectory. In some embodiments, the first trajectory varies both positively and negatively upon an axis perpendicular to the cross-sectional two-dimensional plane of rotation of the first rotational robotic. In some embodiments, each line detector has a height at least an order of magnitude larger than its width. In some embodiments, the first rotational apparatus comprises a platform suspended from a vertically superior railing by which travel of x-ray generation assembly along the first trajectory is enacted. In some embodiments, the first rotational apparatus comprises a robotically controlled supporting platform by which travel of x-ray generation assembly along the first trajectory is enacted. In some embodiments, the second trajectory has a smaller average radius than the first trajectory. In some embodiments, the rotational collimator is configured to rotate about an axis of rotation on the first trajectory and perpendicular to the first trajectory. In some embodiments, the first trajectory comprises a non-linear ovoid plane. In various embodiments, the beam of x-ray photons incident on the x-ray detector comprises, in total, less than 20%, less than 15%, less than 10%, less than 5%, or less than 1% scattered photons. In some embodiments, the target is an anatomical target. In further embodiments, the anatomical target is a human extremity. In other embodiments, the anatomical target is a human breast. In yet other embodiments, the anatomical target is an entire human body.

In yet another aspect, disclosed herein are methods of performing plural-plane narrow-beam computed tomography (CT) to image a target, the method comprising: generating, by a first x-ray generation assembly, a collimated narrow beam of x-ray photons, the first x-ray generation assembly affixed to a first rotational apparatus configured to rotate on a first trajectory at a first rotational speed and comprising an x-ray tube and a rotational collimator; generating, by a second x-ray generation assembly, a collimated narrow beam of x-ray photons, the second x-ray generation assembly affixed to a second rotational apparatus configured to rotate on a second trajectory at a second rotational speed and comprising an x-ray tube and a rotational collimator; detecting, by an x-ray detection assembly, the narrow beams of x-ray photons, the x-ray detection assembly affixed to a third rotational apparatus configured to rotate on a third trajectory at a third rotational speed, wherein the x-ray detection assembly is mechanically decoupled from the first and second rotational apparatuses and comprises at least one line detector; and performing, by a controller unit, operations comprising: controlling the first rotational apparatus to rotate the first x-ray generation assembly on the first trajectory at the first rotational speed; controlling the second rotational apparatus to rotate the second x-ray generation assembly on the second trajectory at the second rotational speed; controlling the third rotational apparatus to rotate the x-ray detection assembly on the third trajectory at the third rotational speed, around a target; and controlling the speed and phase of rotation of the rotational collimator of the first and second x-ray generation assemblies and the speed and phase of rotation of the x-ray detection assembly such that primary x-ray photons of the narrow beams generated by the first and second x-ray generation assemblies become incident upon the at least one line detector; wherein the first trajectory comprises a rotation of at least 90 degrees plus one-half fan-angle, wherein the second trajectory comprises a rotation of at least 90 degrees plus one-half fan-angle, and wherein the third trajectory comprises more than 360 degrees rotation. In some embodiments, each line detector has a height at least an order of magnitude larger than its width. In various embodiments, the beams of x-ray photons incident on the x-ray detector comprises, in total, less than 20%, less than 15%, less than 10%, less than 5%, or less than 1% scattered photons. In some embodiments, the target is an anatomical target. In further embodiments, the anatomical target is a human extremity. In other embodiments, the anatomical target is a human breast. In yet other embodiments, the anatomical target is an entire human body.

BRIEF DESCRIPTION OF THE DRAWINGS

A better understanding of the features and advantages of the present subject matter will be obtained by reference to the following detailed description that sets forth illustrative embodiments and the accompanying drawings of which.

DETAILED DESCRIPTION

Figure 1A:
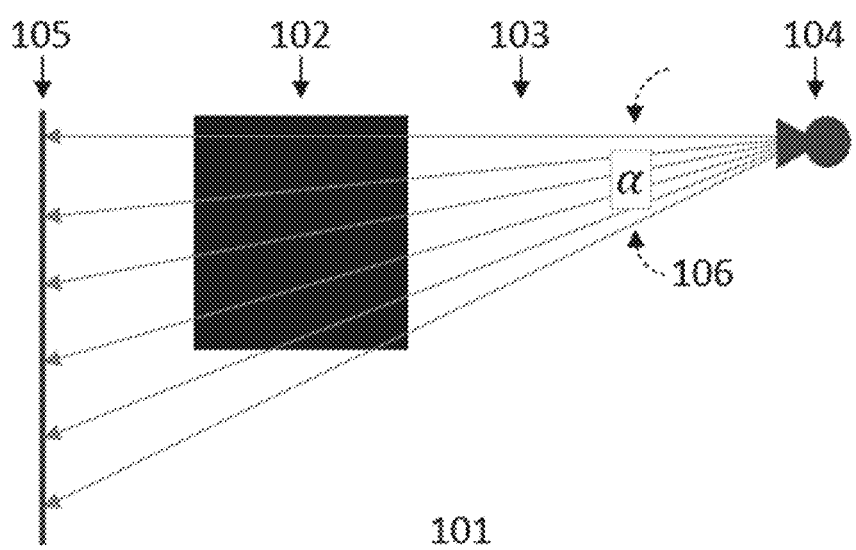
FIGS. 1A-1C are side-view, perspective-view, and schematic-view of the Flat-Plane Narrow-Beam CT image acquisition apparatus and methodology.
Figure 1B:
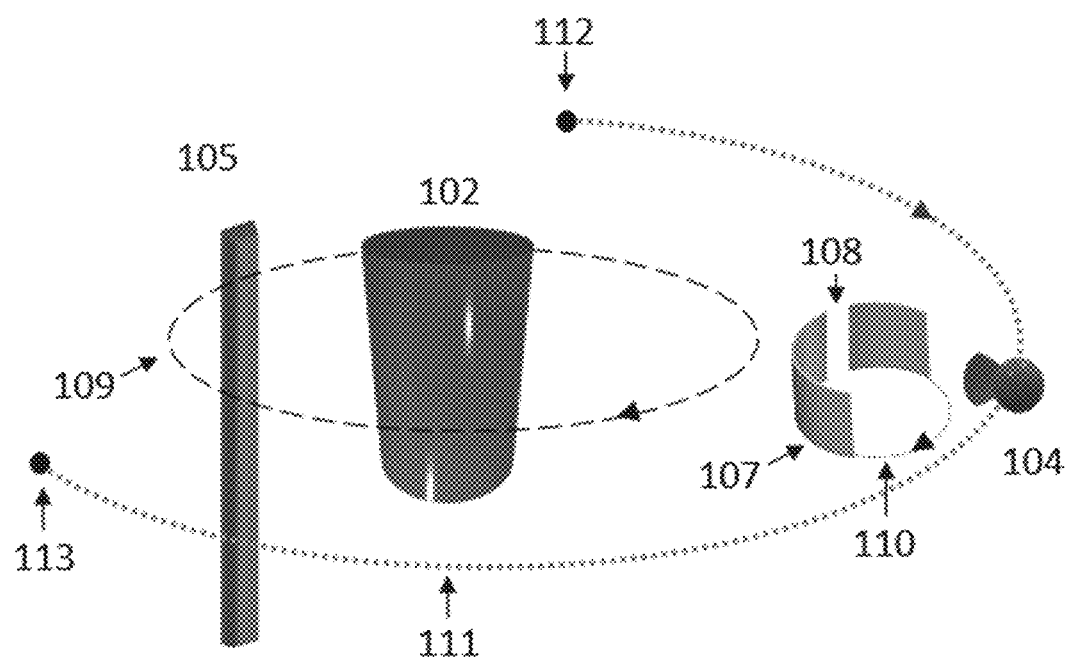

Described herein, in certain embodiments, are plural-plane narrow-beam computed tomography (CT) systems comprising: an x-ray generation assembly affixed to a first rotational apparatus configured to rotate on a first trajectory at a first rotational speed, the x-ray generation assembly comprising at least one x-ray tube and a rotational collimator associated with each x-ray tube, the x-ray generation assembly configured to generate a narrow collimated narrow beam of x-ray photons having a fan angle of less than 5.8 degrees; an x-ray detection assembly affixed to a second rotational apparatus configured to rotate on a second trajectory at a second rotational speed, wherein the x-ray detection assembly is mechanically decoupled from the first rotational apparatus and comprises at least one line detector configured to detect the narrow beam of x-ray photons, wherein the line detectors of the x-ray detection assembly operate in time-delay-integration mode; and a controller configured to perform at least: controlling the first rotational apparatus to rotate the x-ray generation assembly on the first trajectory at the first rotational speed; controlling the second rotational apparatus to rotate the x-ray detection assembly on the second trajectory at the second rotational speed, around a target; and controlling the speed and phase of rotation of the rotational collimator and the speed and phase of rotation of the x-ray detection assembly such that primary x-ray photons within the narrow beam of x-ray photons become incident upon the at least one line detector; wherein the second rotational speed is at least 10 times higher than the first rotational speed, wherein the first trajectory and the second trajectory are non-coplanar, wherein the first trajectory comprises less than 360 degrees rotation, and wherein the secondary trajectory comprises more than 360 degrees rotation.

Also described herein, in certain embodiments, are plural-plane narrow-beam computed tomography (CT) systems comprising: a first x-ray generation assembly affixed to a first rotational apparatus configured to rotate on a first trajectory at a first rotational speed; a second x-ray generation assembly affixed to a second rotational apparatus configured to rotate on a second trajectory at a second rotational speed; wherein each x-ray generation assembly comprises an x-ray tube and a rotational collimator, and wherein each x-ray generation assembly is configured to generate a narrow collimated beam of x-ray photons; an x-ray detection assembly affixed to a third rotational apparatus configured to rotate on a third trajectory at a third rotational speed, wherein the x-ray detection assembly is mechanically decoupled from the first and second rotational apparatuses and comprises at least one line detector configured to detect the narrow beams of x-ray photons; and a controller configured to perform at least: controlling the first rotational apparatus to rotate the first x-ray generation assembly on the first trajectory at the first rotational speed; controlling the second rotational apparatus to rotate the second x-ray generation assembly on the second trajectory at the second rotational speed; controlling the third rotational apparatus to rotate the x-ray detection assembly on the third trajectory at the third rotational speed, around a target; and controlling the speed and phase of rotation of the rotational collimator of the first and second x-ray generation assemblies and the speed and phase of rotation of the x-ray detection assembly such that primary x-ray photons of the narrow beams generated by the first and second x-ray generation assemblies become incident upon the at least one line detector; wherein the first trajectory comprises a rotation of at least 90 degrees plus one-half fan-angle, wherein the second trajectory comprises a rotation of at least 90 degrees plus one-half fan-angle, and wherein the third trajectory comprises more than 360 degrees rotation.

Also described herein, in certain embodiments, are methods of performing plural-plane narrow-beam computed tomography (CT) to image a target, the method comprising: generating, by an x-ray generation assembly, a collimated narrow beam of x-ray photons having a fan angle of less than 5.8 degrees, the x-ray generation assembly affixed to a first rotational apparatus configured to rotate on a first trajectory at a first rotational speed, the x-ray generation assembly comprising at least one x-ray tube and a rotational collimator associated with each x-ray tube; detecting, by an x-ray detection assembly, the narrow beam of x-ray photons, the x-ray detection assembly affixed to a second rotational apparatus configured to rotate on a second trajectory at a second rotational speed, wherein the x-ray detection assembly is mechanically decoupled from the first rotational apparatus and comprises at least one line detector, and wherein the at least one line detector operates in time-delay-integration mode; and performing, by a controller unit, operations comprising: controlling the first rotational apparatus to rotate the x-ray generation assembly on the first trajectory at the first rotational speed; controlling the second rotational apparatus to rotate the x-ray detection assembly on the second trajectory at the second rotational speed, around a target; and controlling the speed and phase of rotation of the rotational collimator and the speed and phase of rotation of the x-ray detection assembly such that primary x-ray photons within the narrow beam of x-ray photons become incident upon the at least one line detector; wherein the second rotational speed is at least 10 times higher than the first rotational speed, wherein the first trajectory and the second trajectory are non-coplanar, wherein the first trajectory comprises less than 360 degrees rotation, and wherein the secondary trajectory comprises more than 360 degrees rotation.

Also described herein, in certain embodiments, are methods of performing plural-plane narrow-beam computed tomography (CT) to image a target, the method comprising: generating, by a first x-ray generation assembly, a collimated narrow beam of x-ray photons, the first x-ray generation assembly affixed to a first rotational apparatus configured to rotate on a first trajectory at a first rotational speed and comprising an x-ray tube and a rotational collimator; generating, by a second x-ray generation assembly, a collimated narrow beam of x-ray photons, the second x-ray generation assembly affixed to a second rotational apparatus configured to rotate on a second trajectory at a second rotational speed and comprising an x-ray tube and a rotational collimator; detecting, by an x-ray detection assembly, the narrow beams of x-ray photons, the x-ray detection assembly affixed to a third rotational apparatus configured to rotate on a third trajectory at a third rotational speed, wherein the x-ray detection assembly is mechanically decoupled from the first and second rotational apparatuses and comprises at least one line detector; and performing, by a controller unit, operations comprising: controlling the first rotational apparatus to rotate the first x-ray generation assembly on the first trajectory at the first rotational speed; controlling the second rotational apparatus to rotate the second x-ray generation assembly on the second trajectory at the second rotational speed; controlling the third rotational apparatus to rotate the x-ray detection assembly on the third trajectory at the third rotational speed, around a target; and controlling the speed and phase of rotation of the rotational collimator of the first and second x-ray generation assemblies and the speed and phase of rotation of the x-ray detection assembly such that primary x-ray photons of the narrow beams generated by the first and second x-ray generation assemblies become incident upon the at least one line detector; wherein the first trajectory comprises a rotation of at least 90 degrees plus one-half fan-angle, wherein the second trajectory comprises a rotation of at least 90 degrees plus one-half fan-angle, and wherein the third trajectory comprises more than 360 degrees rotation.

Figure 3:
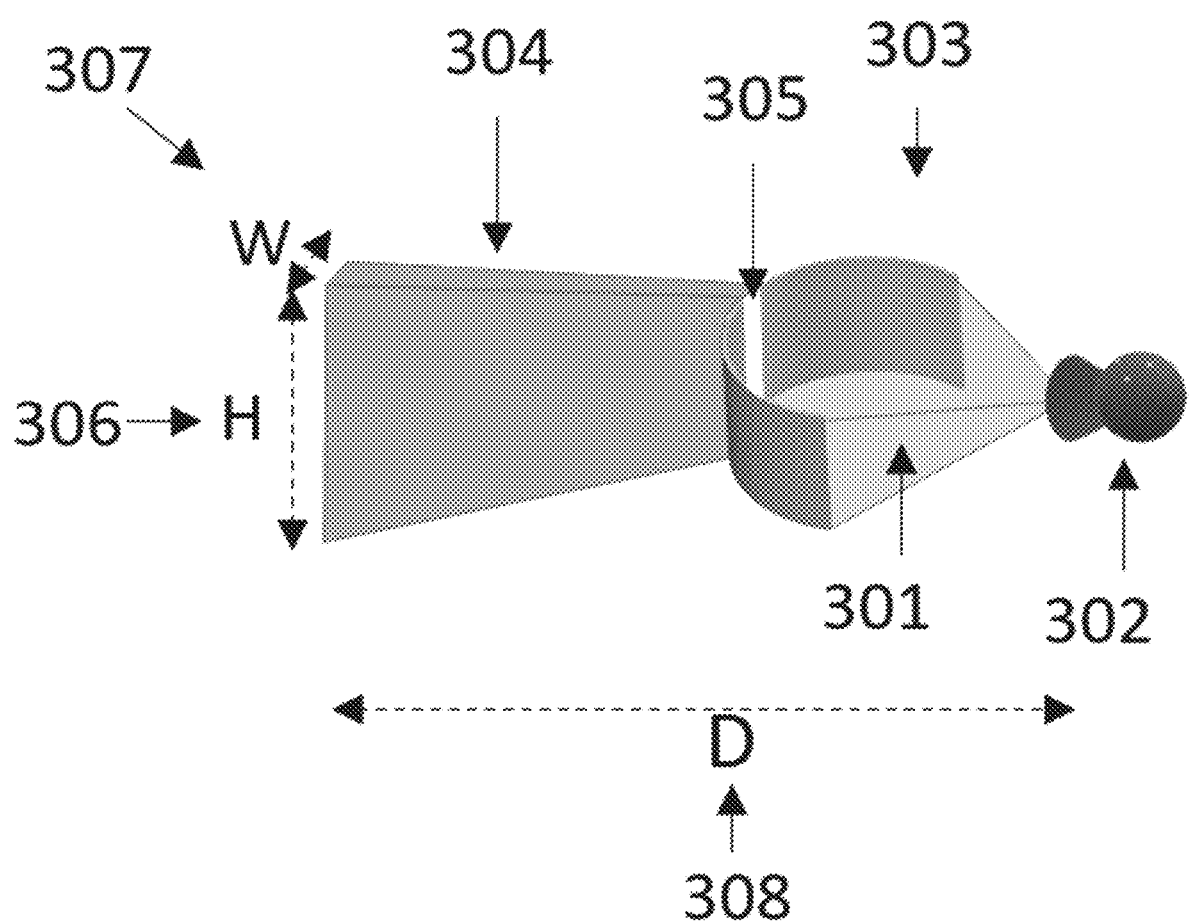
FIG. 3 shows the collimation of x-rays in generating the narrow-beam.

In all the embodiments of the disclosed subject matter, at any instance of time during an x-ray exposure, the x-ray beam that interacts with the object of interest has a substantially elongated shape. This beam is hereinafter referred to as "Narrow-Beam." The specificities of the Narrow-Beam are shown in FIG. 3. During an exposure in Plural-Plane Narrow-Beam CT, an x-ray beam 301 is generated in an x-ray source 302, such as an x-ray tube. The generated beam, then, is substantially collimated in a collimator 303, to form a narrow beam 304. Here, the collimation entails stopping all the x-ray photons within the sourced beam 301 within the collimator 303, except for the photons that are aligned with an opening 305 within the collimator, where the photons can exit the collimator structure 303. The shape of the resulting narrow beam 304 can be described with two parameters: its height, denoted as parameter H 306, and its width, denoted as parameter W 307, at the time of interaction with the sensitive area of the x-ray detector. The magnitude of the height 306 of the narrow beam is dependent on the cone-angle coverage of the narrow beam. Similarly, the magnitude of the width 307 of the narrow beam is dependent on the fan-angle coverage of the narrow beam. In Plural-Plane Narrow-Beam CT, the fan angle coverage of the narrow beam is substantially smaller than its cone angle coverage. The difference between the fan and cone angles is dependent on the size of the utilized x-ray detector (not shown in FIG. 3). In Plural-Plane Narrow-Beam CT, there is a substantial difference between the height and width of the utilized x-ray detectors. More specifically, the height of the detectors is an order of magnitude larger than its width. In Plural-Plane Narrow-Beam CT, all the primary photons within the narrow beam are incident on the sensitive area of the detector. Therefore, the fan angle coverage of the narrow beam is at least an order of magnitude smaller than its cone angle. Accordingly, the width 307 of the narrow beam is at least an order of magnitude smaller than its height 306. As a numerical example, if the width of the sensitive area of the x-ray detector is 1 centimeter, then its height is at least 10 centimeters. Similarly, the width 307 of the narrow beam has to be at least ten times smaller than its height 306:

$$W \times 10 \leq H \qquad \text{Equation 2.}$$

Another specificity of the shape of the narrow beam is its fan angle coverage. As stated above, the narrow beam in all embodiments of this invention is substantially narrow. In other words, the narrow beam has a substantially smaller fan angle coverage than its cone angle coverage. To put it more concretely, if the distance between the x-ray source 302 and the x-ray detector (not shown in FIG. 3) is denoted as D 308, then:

$$W \times 10 \leq D \qquad \text{Equation 3.}$$

If the fan angle coverage of the narrow beam is denoted as β, with the parameters introduced in FIG. 3, then:

$$\beta = 2 \times \arctan\left(\frac{W/2}{D}\right). \qquad \text{Equation 4}$$

Incorporating the limitations defined in Equation 3 into Equation 4 yields an upper boundary for the fan angle coverage of the narrow beam. To put it more concretely, the fan angle coverage of the narrow beam in all embodiments of this invention is less than 5.8 degrees.

The specific shape of the narrow beam implies that it has a much larger cone-angle coverage than its fan-angle. Therefore, in order to measure the object during a source view angle, the detector must physically move across the object to fully measure it using x-rays. During this movement, the narrow beam sweeps the object. In Plural-Plane Narrow-Beam CT, the detector rotates around the object at a rotational velocity of tens, or even hundreds of, rotations per minute. In Plural-Plane Narrow-Beam CT, the detector operates in time-delay-integration (TDI) mode. This is to mitigate motion blurring that may arise from acquisition occurring during the detector's physical rotation and to compensate for the delay between x-ray capture and line-assembly at the detector. In TDI mode, the charge collected in each line is passed on to the adjacent line within the detector. The passed-on charge, then, is added to the charge that is now being collected in the new line. This simultaneous transfer and accumulation of the acquired signal continues until a specific number of lines participate in this process. At that point, an output line is formed and transferred to a receiver outside of the detector. The most critical parameter in implementing the time-delay-integration strategy is the speed of transferring the accumulated charges. In Plural-Plane Narrow-Beam CT, the charge hand-off speed must be equal to the tangential speed of detector as it rotates around the object. As a numerical example, if the detector around the object on a planar circular path with radius of 10 centimeters, at a rotational speed of 1 rotation per second, then the tangential speed of detector's movement is 10×2×π=62.8 centimeters per second. If the size of each element of the detector is 0.1 millimeter (0.01 centimeters), then the charge-hand-off speed of the TDI mode in Plural-Plane Narrow-Beam CT must be set to $$\frac{62.8}{0.01} = 6280$$

lines per second.

The standard output of a TDI-operating detector is a 1-dimensional line. The overall data of the acquired line contains all the data inside of the lines that the x-ray detector unit contains. As a numerical example, if the x-ray detector has 16 columns of x-ray sensitive lines, then in TDI mode, the charges of the 16 columns are added up and are outputted as one single line information. Such a TDI-enabled detector that output 1-dimensional data is referred to hereinafter as a "line-detector." Plural-Plane Narrow-Beam CT utilizes line-detectors.

It should be noted that tomographic imaging in CT implies acquiring projections from different view angles. In order to fully sample the object of interest, the x-ray source must rotate around the object with a coverage of at least 180 degrees plus the object's fan angle coverage. During this movement, a certain number of projections are made. In this context, each projection is defined as exposing the entire fan angle coverage of the object at a given positioning of the x-ray source. In Plural-Plane Narrow-Beam CT, because the detector has substantially limited coverage along the fan angle, the detector position must change such that it moves around the object being imaged to capture a single complete projection of that object. In other words, each full projection is acquired per full rotation of the x-ray detector around the object. As a numeral example, if the goal of an image acquisition procedure was to acquire 360 projections per each rotation of the x-ray source around the object, then detector must rotate 360 times to capture 360 projections.

Generally, in CT, a prominent mechanical structure which is referred to as a "Gantry" serves to mechanically lock the x-ray source and the detector to one another, facilitating their synchronized rotations during image acquisition. In Plural-Plane Narrow-Beam CT, however, given the substantial difference between the rotational speed of the x-ray source and x-ray detector units these structures are not, and cannot be, mechanically locked to one another by means of a common secondary mechanical structure such as a Gantry. In Plural-Plane Narrow-Beam CT, the x-ray source and x-ray detection units are mechanically decoupled. A central synchronizing mechanical structure such as a gantry, therefore, is not a fundamental design requisite. Plural-Plane Narrow-Beam CT can be implemented as a "Gantry-free" rendition of CT.

A key feature of Plural-Plane Narrow-Beam CT, as described previously, is that the motion trajectory of the x-ray source around the object cannot be confined to a single, flat, 2-dimensional plane. Rather, the motion trajectory of the x-ray unit can be described as moving along a 3-dimensional plane trajectory, or a trajectory that results from the summation of multiple, differing, 2-dimensional planes. Hence, the present subject matter is referred to as "Plural-Plane Narrow-Beam CT."

First Exemplary Embodiment

Figure 4A:
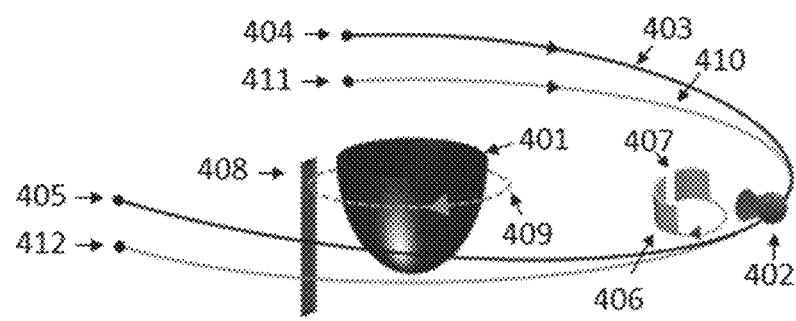
FIGS. 4A-4C shows different views of the first embodiment of Plural-Plane Narrow-Beam CT.
Figure 4B:
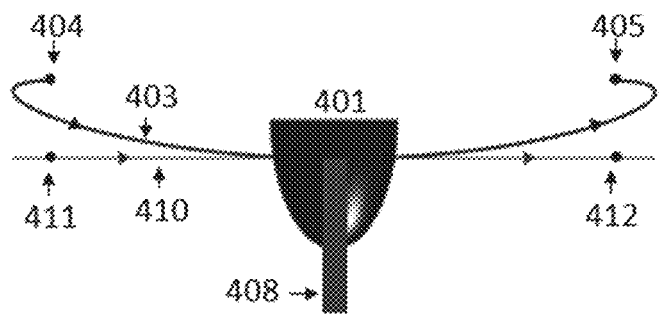
Figure 4C:
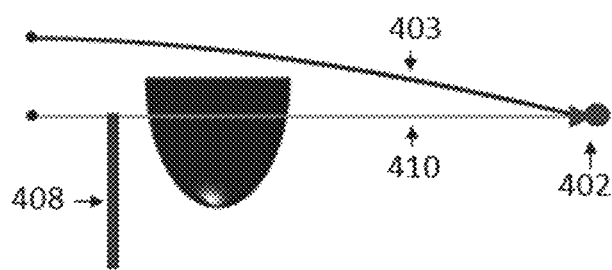

FIGS. 4A-4C illustrate an embodiment of the Plural-Plane Narrow-Beam CT. Here, an object 401 is the object of interest to be imaged. Distinct trajectories among and between hardware elements, to image the object of interest, are described. During Plural-Plane Narrow-Beam CT, an x-ray source 402 rotates along a path 403 around the object 401 from a starting point 404 to a finish point 405. This path 403 travels along a plane that is not 2-dimensional and flat, but rather is 3-dimensional and contoured. A collimator 406 travels with the x-ray source 402. The collimator 406 blocks all the photons generated at the x-ray source 402, excepting those photons that opening 407 within the collimator 406 makes possible for them to pass through. The beam that results subsequent to passage through opening 407 is a narrow beam as described above. The x-ray photons that comprise the narrow beam interact with the object 401 and are subsequently absorbed in the x-ray detector 408. Because Plural-Plane Narrow-Beam CT utilizes line-detectors which hence, have limited fan angle coverage, the detector 408 must rotate around the object 401 along a planar circular path 409 to acquire a complete tomographic projection of object 401. The circular motion of detector 408 is synchronized to the circular motion of the opening 407 of the collimator 406 such that in each view angle of the x-ray source 402, the narrow beam sweeps the entire object and measures it using x-rays. Two side views of this embodiment are shown in FIG. 4B and FIG. 4C. As a comparison, the path that an x-ray source takes in a Flat-Plane Narrow-Beam CT apparatus and method of imaging is overlaid in FIGS. 4A-4C, where the source 402 travels along a 2-dimensional path 410 from a start point 411 to a finish point 412.

Figure 5:
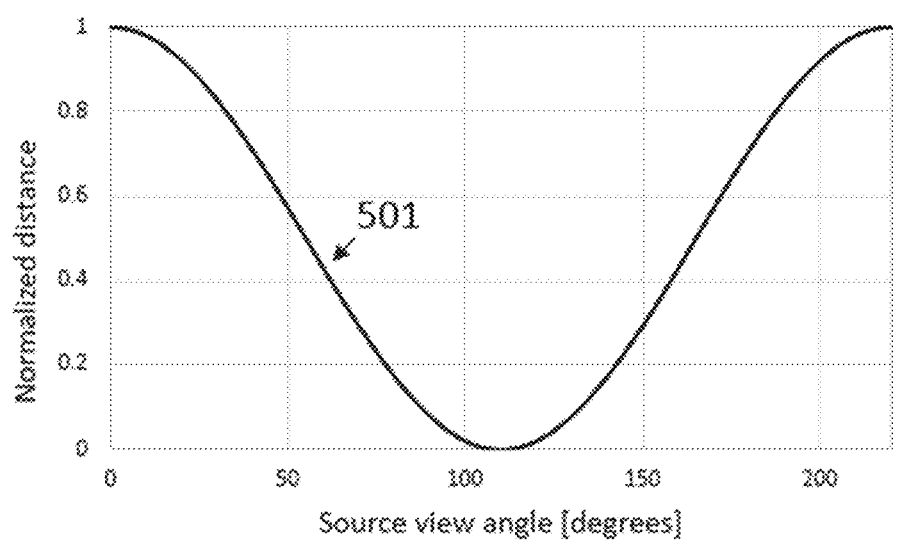
FIG. 5 shows the difference between the trajectories of the source in Flat-Plane Narrow-Beam CT and that of the Plural-Plane Narrow-Beam CT.

The 3-dimensional path 403 of an x-ray source shown in FIGS. 4A-4C is an example of the trajectory of the x-ray source in Plural-Plane Narrow-Beam CT. While discrete subsets of the trajectory might be described as traveling upon a 2-dimensional plane, the overall trajectory required to image object 401 cannot be described as 2-dimensional. It should be understood that the distance between the 2-dimensional (flat-plane) trajectory 410 and the 3-dimensional (plural-plane) trajectory 403 is not constant. Moreover, this distance is non-linear. The graph shown in FIG. 5 provides a visualization of the non-constant and non-linearity of this distance. This graph was generated by measuring the distance between the x-ray sources along the two 2-dimensional plane path 410 and the complex or "plural-plane" path 403 shown in FIGS. 4A-4C. As is shown, the distance 501 between the positioning of the x-ray source in each of the trajectories has a magnitude that changes non-linearly with the change in source view angle. Therefore, the movement path of the x-ray source in its entirety in Plural-Plane Narrow-Beam cannot be described as a single 2-dimensional (flat) plane. This property, namely the complex movement of the x-ray source around the object, is an underlying principle of Plural-Plane Narrow-Beam CT image acquisition geometry.

Figure 1C:
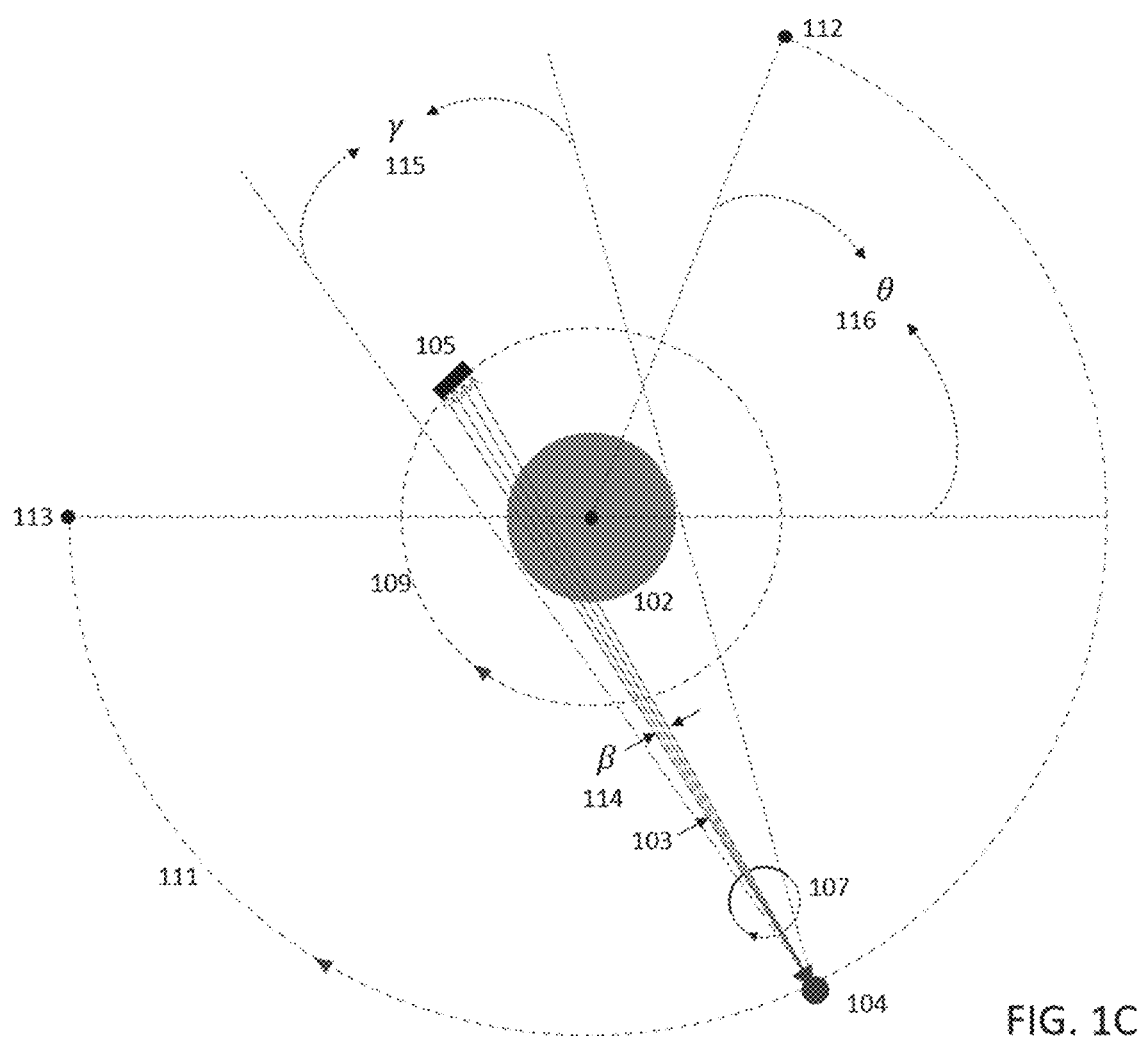

According to FIGS. 4A-4C, it should be understood that the movement path 403 of the x-ray source 402 in Plural-Plane Narrow-Beam CT varies with respect to any cross-sectional 2-dimensional plane, such as the one shown in FIG. 1C. More concretely, as the x-ray source 402 rotates the object 401, it traverses into and out of the 2-dimensional cross-sectional plane both negatively and positively. Therefore, the movement path 403 of the x-ray source 402 in Plural-Plane Narrow-Beam CT cannot be achieved through a simple spiral motion of the source around the object of interest.

In the Plural-Plane Narrow-Beam CT system shown in FIGS. 4A-4C, while the cross-sectional movement path of the detector 408 is depicted and described as strictly circular, the moving path of the x-ray source 402 around the object 401 need not be. As long as the x-ray source 402 measures the object of interest while rotating at least (180 degrees+fan angle) around the object, it is possible to generate reconstruct 3-dimensional CT images with isotropic voxels. In other words, the radial distance between the object and the x-ray source can change during a scan, as long as the entire fan angle coverage of the object at that particular radial distance is measured.

Despite the complex movement of the x-ray source in the embodiment disclosed in FIGS. 4A-4C, the cross-sectional motion path of the x-ray detector 408 around the object of interest remains the same. This is made possible because of the gantry-free principle of the Plural-Plane Narrow-Beam CT apparatus. Because a large centralized structural component for synchronization of the x-ray source and detector are not required in Plural-Plane Narrow-Beam CT, the movement of the x-ray source does not automatically result in the movement of the x-ray detector. These two units, the x-ray source and detector, are mechanically decoupled. This fundamental feature of Plural-Plane Narrow-Beam CT enables flexible control of the movements of the x-ray source that do not necessarily have an impact on the movement of the detector. At any instance of time, a distinct controller unit controls the movements of the x-ray source, detector or detectors, and the exposure sequences.

Figure 2:
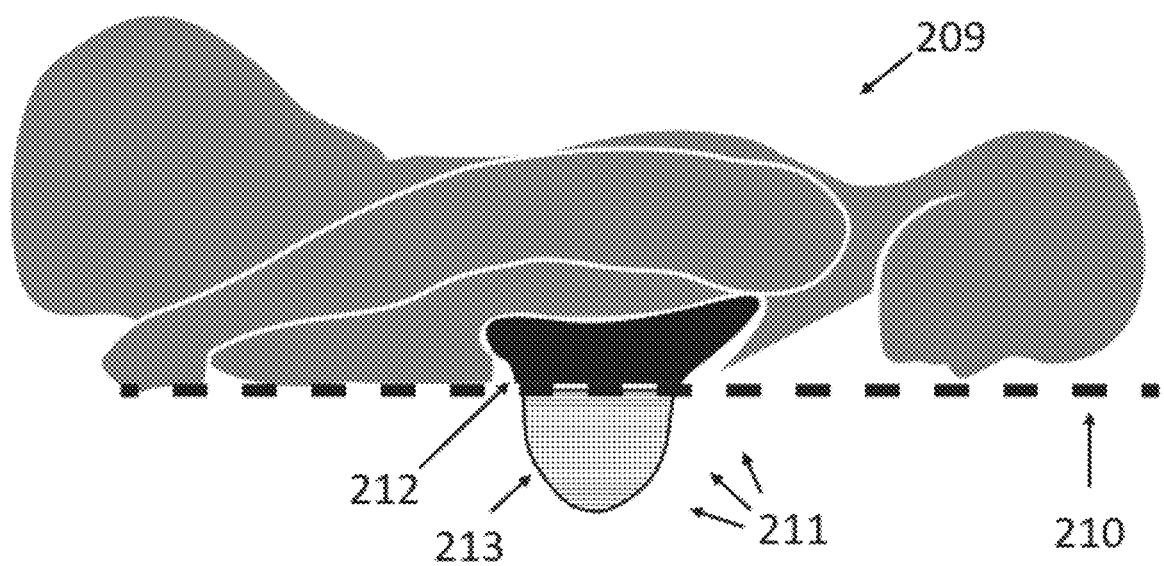
FIG. 2 illustrates the coverage that results from utilization of Flat-Plane Narrow-Beam CT for imaging a complex-shaped object.
Figure 6A:
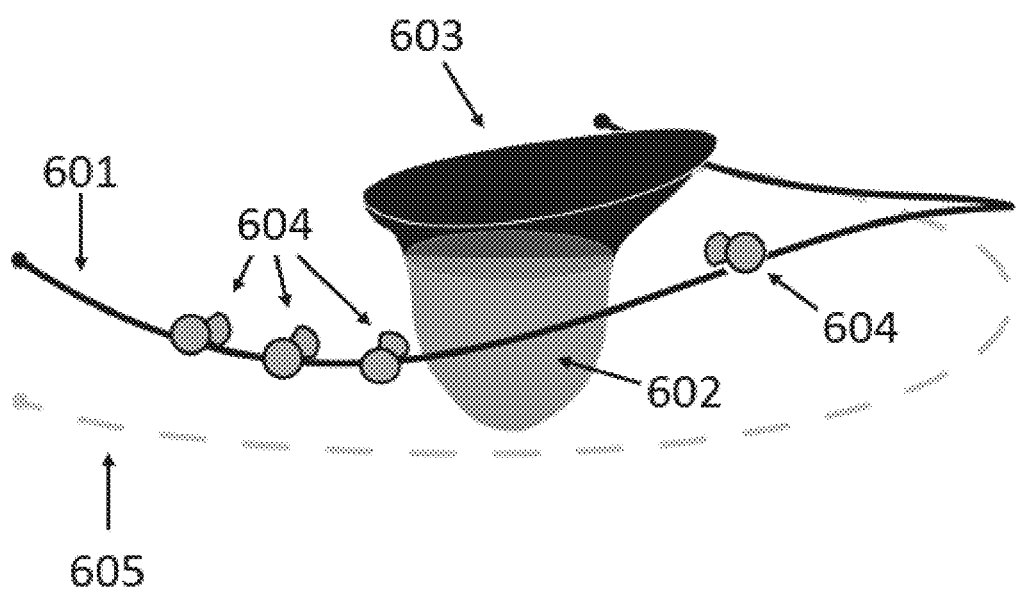
FIGS. 6A and 6B shows the considerable gain in complex-object coverage achieved with a complex x-ray source trajectory in Plural-Plane Narrow-Beam CT.
Figure 6B:
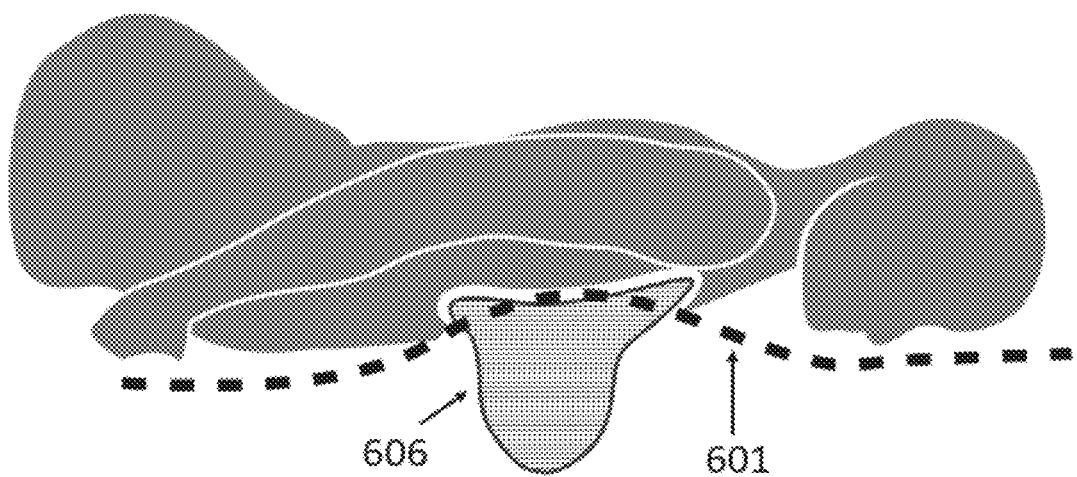

If an object is scanned using the Plural-Plane Narrow-Beam CT image acquisition geometry shown in FIGS. 4A-4C, not all the voxels of the resulting CT image will be isotropic. This critical point is visually illustrated in FIGS. 6A and 6B. Here, similar to the case shown in FIG. 3B, the object of interest is the breast of a female human. A perspective view of only the breast tissue is shown in FIG. 6A, and a side view of the positioning of the patient is shown in FIG. 6B (just as was shown in FIG. 2). As initially shown in FIG. 2 and as shown in FIG. 6B the breast 606 has a complex shape. In FIG. 6A (also see FIG. 2), that complex shape is partitioned into an anterior region 602 and posterior region 603, showing the region of such a complex shape that can be imaged with Flat-Plane Narrow-Beam CT versus that which can be imaged with Plural-Plane Narrow-Beam CT. Note that in FIG. 6A the x-ray source 604 is depicted in multiple positions, demonstrating its moving location as it rotates around the breast along the complex plural-plane trajectory 601. The x-ray source trajectory of Flat-Plane Narrow-Beam CT 605 is also shown. Trajectory 605 is shown as a gray dashed line and breast region 602 is shown in gray as well to illustrate that the field-of-view created by trajectory 605 results in capturing region 602 of the breast anatomy but not region 603. The complex trajectory 601 in this embodiment of Plural-Plane Narrow-Beam CT, on the other hand, allows for a field-of-view that encompasses both region 602 and region 603 of the breast anatomy. This point is further reinforced in FIG. 6B in which curved line 601 shows a simplified side-view of a plural-plane x-ray source trajectory which results in encompassing the complex shape of the breast 606 within its field-of-view.

A fully isotropic CT image means that in all the voxels of the CT image, all sides are the same dimension in orthogonal cartesian planes. Accordingly, in the embodiment of Plural-Plane Narrow-Beam CT shown in FIG. 6A the posterior region 603 of the breast tissue is measured only during a portion, not all, of the rotation of the x-ray source 604 around the breast 601. The anterior region 602; however, is fully measured. In other words, the posterior regions of the breast anatomy are measured semi-tomographically, while the rest of the breast, including its anterior region, is imaged tomographically. The limited angle tomographic imaging is commonly referred to as tomosynthesis imaging. Therefore, in the Plural-Plane Narrow-Beam CT embodiment shown in FIGS. 6A and 6B, the reconstructed CT image will contain voxels that are semi-isotropic in the posterior region, and fully isotropic in the rest of the breast. Due to the combined tomosynthesis and tomographic nature of this image acquisition mode, this embodiment is referred to as the "Tomo-CT" embodiment of Plural-Planar Narrow-Beam CT.

It should be understood that a critical advantage of using line-detectors in the Plural-Plane Narrow-Beam CT is a major reduction in the level of scattered photons that are acquired by the detector. If fact, the size and the positioning of the detector must be selected such that during an x-ray exposure, the acquired scattered x-ray photons account for less than 10% of the entire x-ray photons acquired by the detector.

Second Exemplary Embodiment

Figure 7:
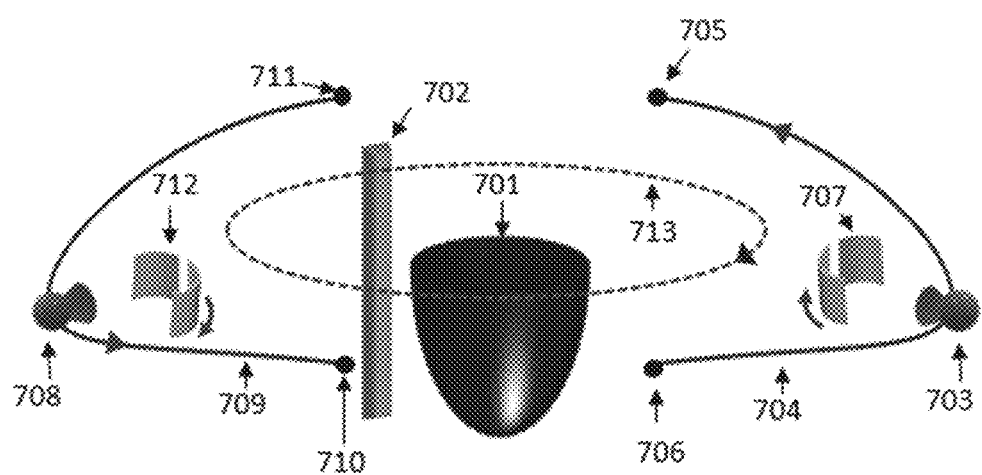
FIG. 7 shows a perspective view of a second embodiment of Plural-Plane Narrow-Beam CT.

FIG. 7 illustrates another embodiment of the Plural-Plane Narrow-Beam CT. In Plural-Plane Narrow-Beam CT, a full measurement of the object in each view angle of the source requires a full rotation of the detector around the object. The collected data during each rotation of the detector are combined to form a single projection. For a successful image reconstruction that results in high-quality CT images, it can be necessary to acquire hundreds, or even thousands, of projections as the x-ray source rotates around the object for at least (180 degrees+fan angle) and at most 360 degrees. As stated previously, in Plural-Plane Narrow-Beam CT, there is a substantial difference between the rotational speed of the x-ray source and the x-ray detector: the detector unit rotates at a rotational velocity that is at least an order of magnitude higher than that of the x-ray unit. For example, if the x-ray source completes a rotation around the object at a speed of 1 rotation per minute (60 seconds), then the rotational speed of the detector unit is at least 1 revolution per 6 seconds. Due to this substantial difference between the rotational speeds of the detector and the x-ray source around the object, these units are mechanically decoupled. With decoupled source and detector, it is possible to image the object of interest using multiple x-ray sources and a single x-ray detector. As shown in FIG. 7, an object 701 is imaged using a single line detector 702, and two x-ray sources. The first x-ray source 703 rotates around the object of interest 701 on a first Plural-Plane trajectory 704 from a start point 705 to a finish point 706. Similar to previous embodiments, a first collimator 707 travels with the first x-ray source 703. The speed of rotation of the collimator 707 is synchronized with the x-ray detector 702 such that the narrow beam that exits the first collimator 707 is fully captured by the x-ray detector 702. On the opposite side of the object of interest 701, a second x-ray source 708 rotates around the object 701 along a plural-plane trajectory 709 from a start point 710 to a finish point 711. A second collimator 712 travels around the object 701 along with the second x-ray source 708. Similar to the first collimator 707, the second collimator 712 rotates in synchrony with the x-ray detector 702 such that the narrow beam that exits the second collimator 712 is always captured by the x-ray detector 702. The x-ray detector 702 continuously rotates around the object 701 on a circular trajectory 713.

Figure 8A:
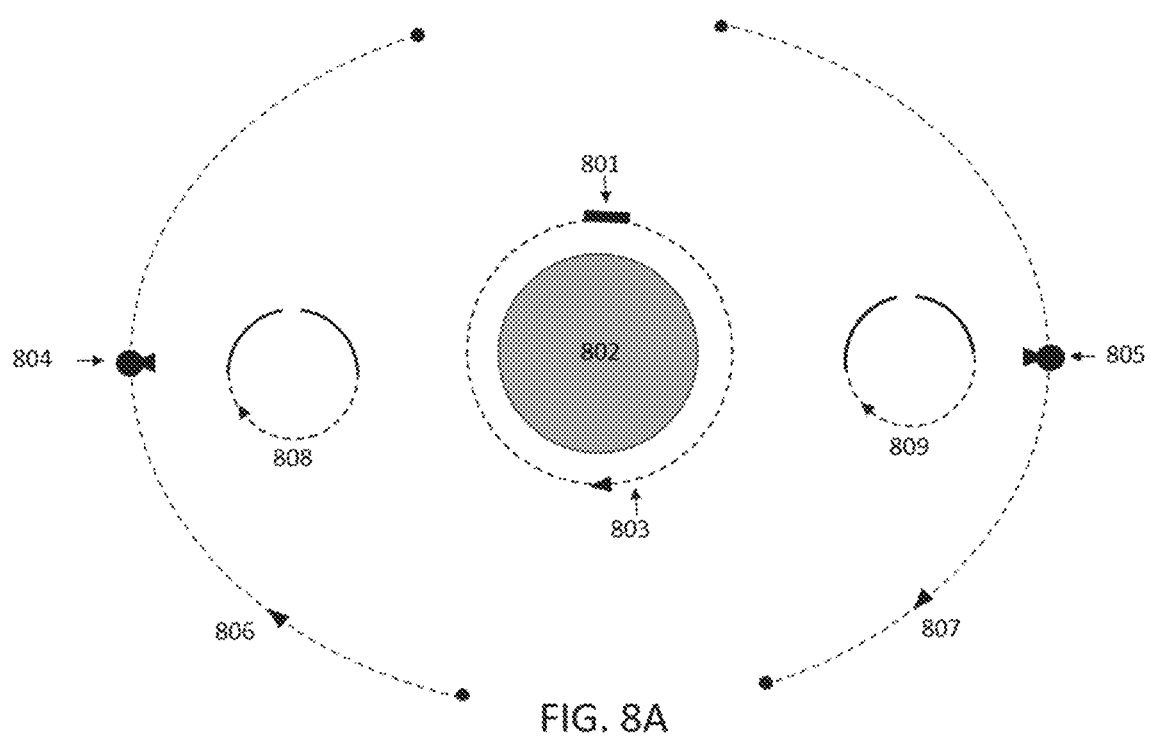
FIGS. 8A-8H illustrate the x-ray exposure sequencing in the second embodiment of Plural-Plane Narrow-Beam CT.
Figure 8B:
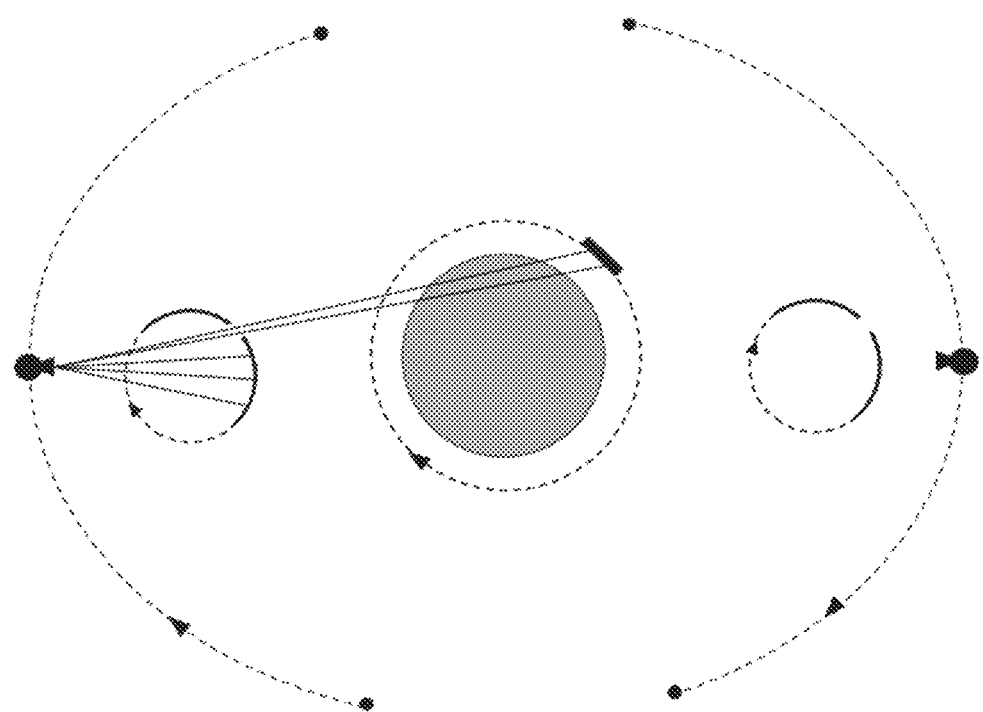
Figure 8C:
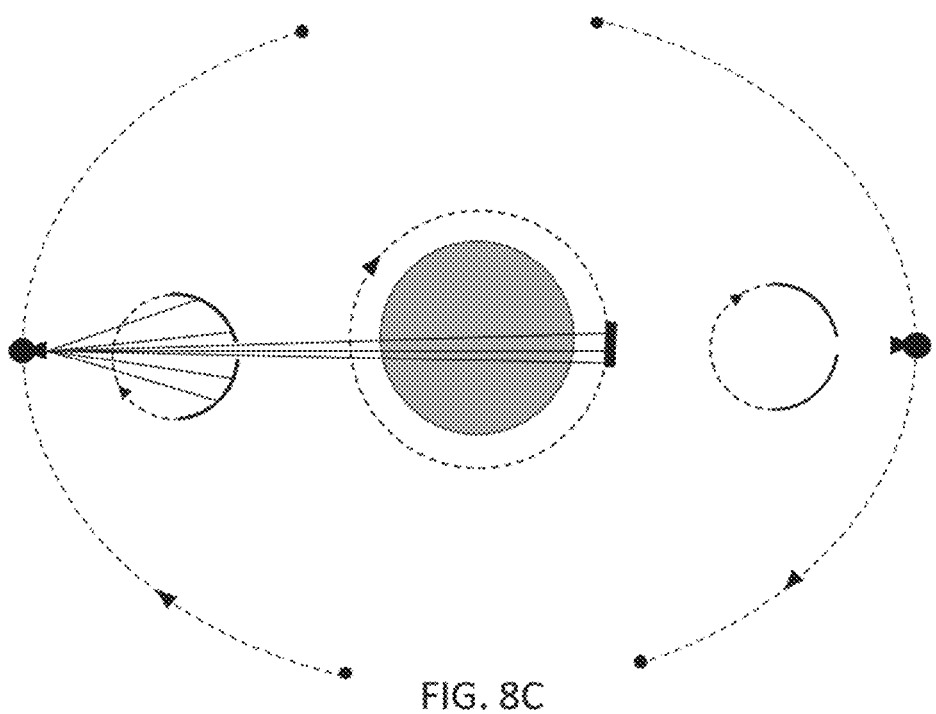
Figure 8D:
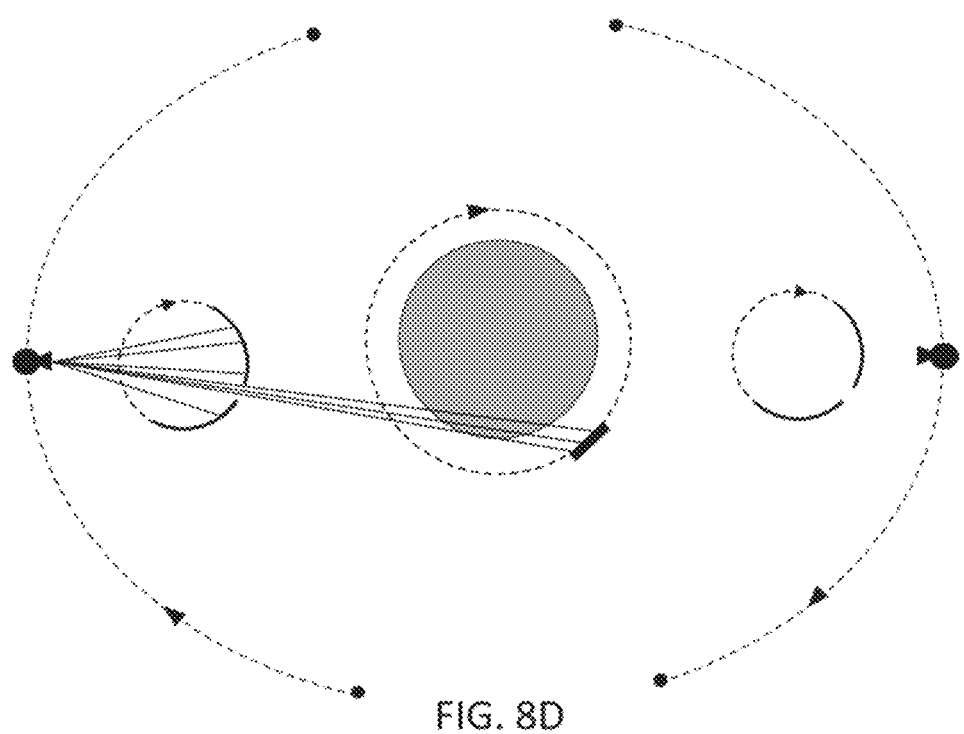
Figure 8E:
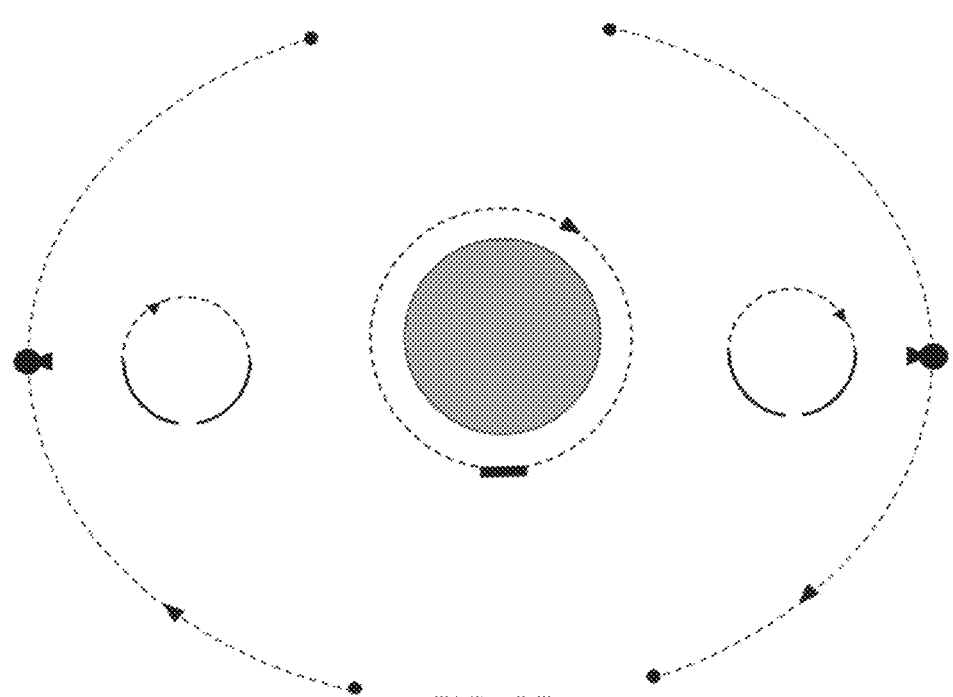
Figure 8F:
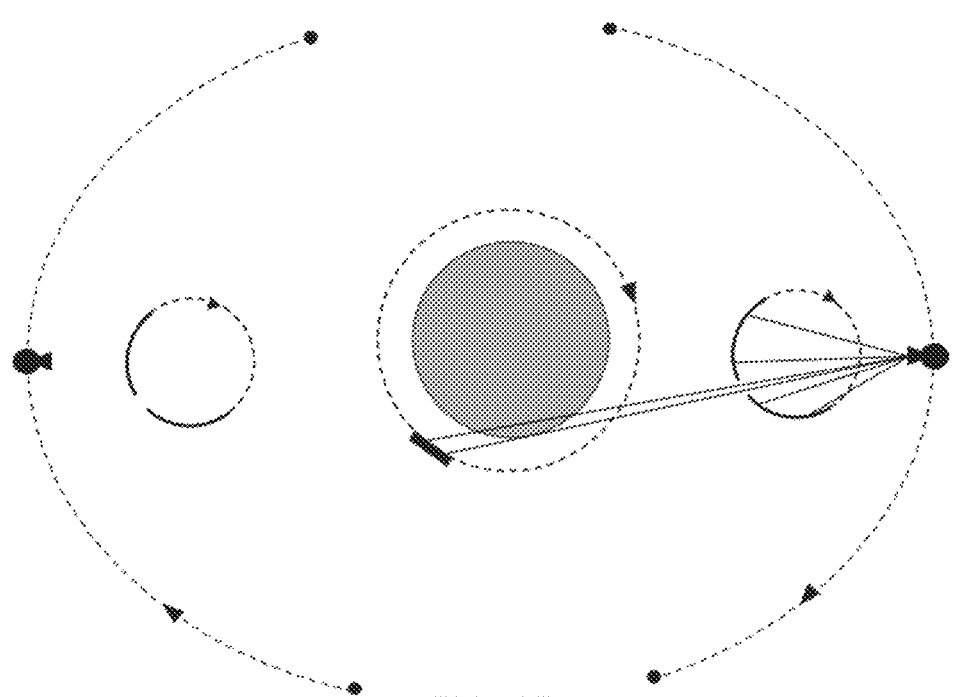
Figure 8G:
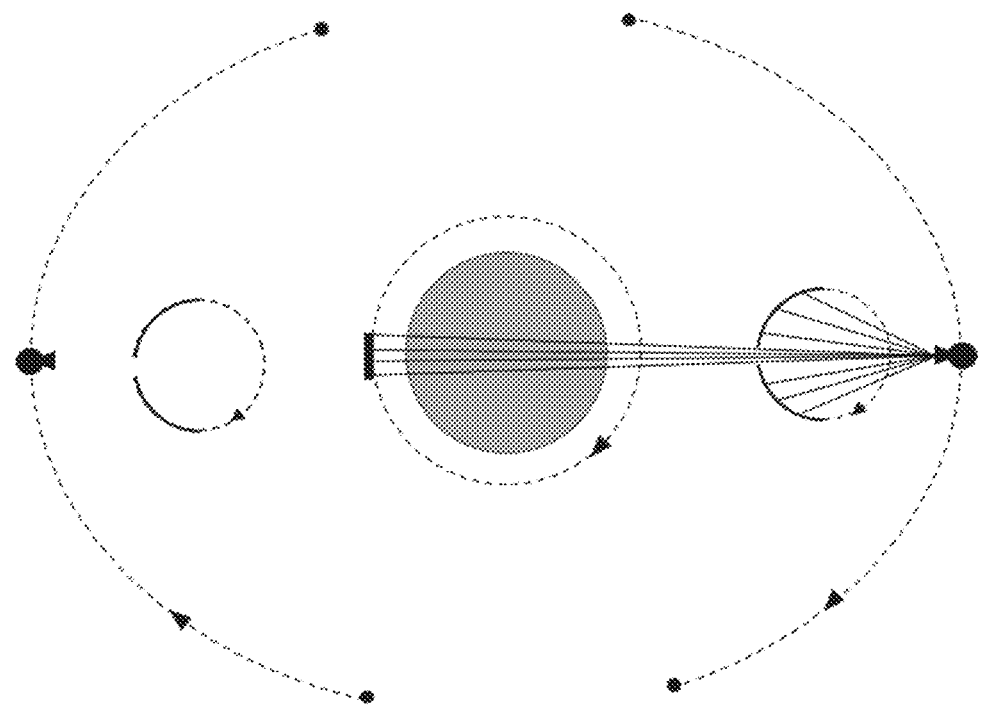
Figure 8H:
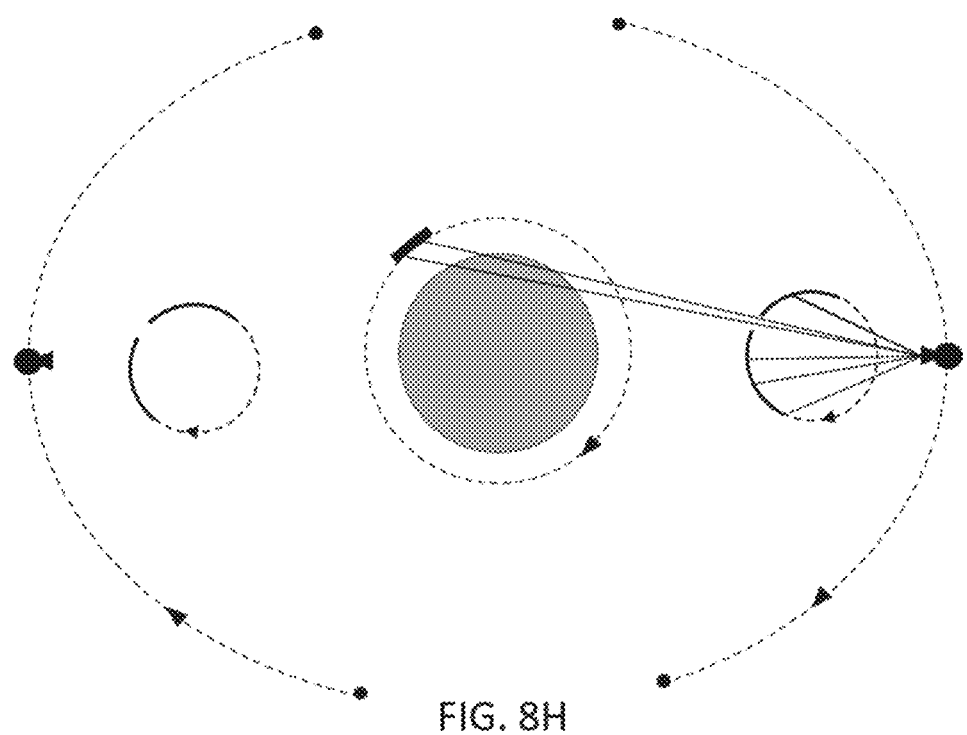

As a single detector can only "face" and hence capture the beam emitted from a single x-ray source at a given instance, yet in this embodiment a single detector captures the generated narrow beams emitted from multiple x-ray sources, the x-ray exposure sequence must be controlled such that each x-ray sources do not generate x-rays at the same time. The exposure sequence is outlined in FIGS. 8A-8H and described in the following. These figures are the planar views of the imaging apparatus at eight instanced of time. Similar to the geometry shown in FIG. 7, a line detector 801 rotates around an object of interest 802 on a circular path 803. At each instance of time during a scan procedure, the first 804 and second 805 x-ray sources travel through their trajectories 806-807, along with the collimators 808-809. In each x-ray source, an x-ray exposure commences whenever there is a line of sight between the x-ray source, the collimator opening, the object and the line detector. The positioning and moving trajectories of the x-ray sources must be selected such that two or more x-ray sources do not generate x-rays at the same time. During each scan, there are periods of time when none of the x-ray sources generate x-rays. FIG. 8A represents such an instance. As different parts of the imaging system rotate, there is an instance of time when the line-of-sight condition for the first x-ray source is met. Such a case is shown in FIG. 8B. At this moment, an x-ray exposure in the first x-ray source is triggered. Therefore, x-rays are generated in the first x-ray source, collimated in the first collimator, interact with the object of interest, and recorded in the detector. The exposure through the narrow beam continues, as shown in FIGS. 8C and 8D, until the line-of-sight disappears. At this point, the first x-ray source stops the x-ray exposure. The rotations of the moving parts of the imaging system continue, as shown in FIG. 8E, until a line-of-sight is established between the second x-ray source, the second collimator opening, the object and the line detector, at which point the second x-ray source transitions to the x-ray exposure mode, as shown in FIG. 8F. The exposure continues with the movements of the moving parts of the imaging system, as shown in FIGS. 8G-8H, until the line-of-sight for the second x-ray source disappears and accordingly, the exposure in the second x-ray source terminates. The cycle outlined in FIGS. 8A-8H continues, until a desired number of projections are acquired. This mode of operation outlined in this embodiment is hereinafter referred to as the multi-source-single-detector mode.

In the multi-source-single-detector imaging mode, the x-ray sources physically transition through their individual plural-plane trajectories as they go through the abovementioned exposure cycle; however, the translational speed of their movements along their trajectories is at least an order of magnitude less than the rotational speed of the detector around the detector. In each rotation of the detector, at least two projections are acquired. The acquired projections can be used in an image reconstruction unit to generate a CT image. The major benefit of multi-source-single-detector imaging mode is its allowance for a reduction in overall required scan time for imaging of an object. For instance, in using the apparatus shown in FIGS. 4A-4C, a scan protocol requires acquiring 60 projections, and the line detector rotates at a speed of 1 rotation per second, then it takes 60 seconds (1 minute) to complete a scan. Using the multi-source-single-detector mode implemented using the setup shown in FIG. 7, the same number of projections can be collected in half the time (30 seconds), resulting in a major reduction in overall scan time.

Third Exemplary Embodiment

Figure 9:
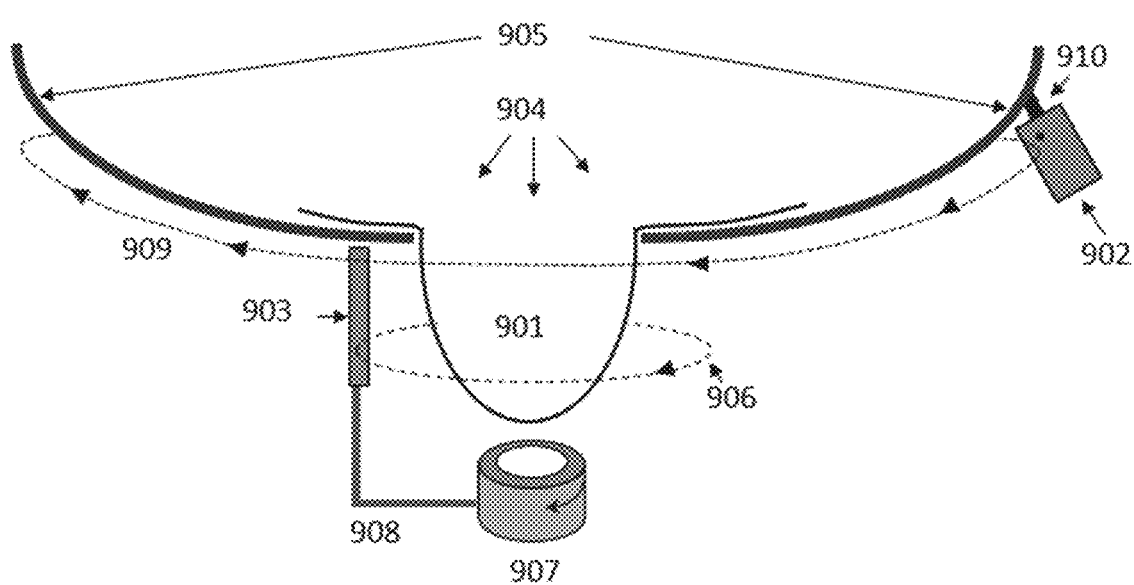
FIG. 9 illustrates a third embodiment of Plural-Plane Narrow-Beam CT.

The combined two main features of the Plural-Plane Narrow-Beam CT (non-2-dimensional moving trajectory of the x-ray source and the mechanical decoupling the x-ray source and detector) allows for flexibility in the design of the electromechanical structure of the CT scanner in scanning complex shaped objects. This constitutes another embodiment of the present subject matter, as shown in FIG. 9. Here, the object of interest 901 is scanned using an x-ray source 902 and an x-ray line detector 903. The object of interest 901 may be attached to a larger physical structure 904, but only the object of interest 901 is placed within the field of view of the CT system. Therefore, the larger physical structure 904 is kept away from the field of view of the CT system using a barrier 905. An example of such a case is when a breast of a female patient is being imaged in a Plural-Plane Narrow-Beam CT system. In this case, the object of interest is breast 901, and barrier 905 is a scanner tabletop (also commonly known as a "patient bed"). As explained in the previous embodiments of subject matter disclosed herein, the x-ray detector 903 rotates around the object of interest 901 on a circular path 906. The rotational motion in FIG. 9 can be made possible through a rotary actuator system 907. The line detector 903 is attached to the actuator system 907 through a robotic arm 908 that enables the line detector 903 to rotate around the object of interest 901. The x-ray source, and the collimator structure that is mechanically attached to it (not shown in FIG. 9), move along a plural-plane path 909 around the object of interest 901. Here, the x-ray source 902 is suspended from the barrier 905. The movement of the x-ray source through its trajectory 909 can be made possible through a suspension track system attached to the barrier 905. The x-ray source 902, in this case, is mounted on the suspension track through a robotic arm 910. Although only one source structure is shown in FIG. 9, it should be noted that if multiple x-ray sources are used in the scanner system (as described in the second embodiment of the present disclosure), multiple suspension track systems can be utilized to enable the multiple-plane motion paths to the x-ray sources.

Certain Definitions

Unless otherwise defined, all technical terms used herein have the same meaning as commonly understood by one of ordinary skill in the art to which the present subject matter belongs.

As used in this specification and the appended claims, the singular forms "a," "an," and "the" include plural references unless the context clearly dictates otherwise. Any reference to "or" herein is intended to encompass "and/or" unless otherwise stated.

Reference throughout this specification to "some embodiments," "further embodiments," or "a particular embodiment," means that a particular feature, structure, or characteristic described in connection with the embodiment is included in at least one embodiment. Thus, the appearances of the phrase "in some embodiments," or "in further embodiments," or "in a particular embodiment" in various places throughout this specification are not necessarily all referring to the same embodiment. Furthermore, the particular features, structures, or characteristics may be combined in any suitable manner in one or more embodiments.

While preferred embodiments of the present subject matter have been shown and described herein, it will be obvious to those skilled in the art that such embodiments are provided by way of example only. Numerous variations, changes, and substitutions will now occur to those skilled in the art without departing from the present subject matter. It should be understood that various alternatives to the embodiments of the present subject matter described herein may be employed in practicing the present subject matter.

What is claimed is:

1. A plural-plane narrow-beam computed tomography (CT) system comprising:
    a) an x-ray generation assembly affixed to a first rotational apparatus configured to rotate on a first trajectory at a first rotational speed, the x-ray generation assembly comprising at least one x-ray tube and a rotational collimator associated with each x-ray tube, the x-ray generation assembly configured to generate a narrow-collimated beam of x-ray photons having a fan angle of less than 5.8 degrees;
    b) an x-ray detection assembly affixed to a second rotational apparatus configured to rotate on a second trajectory at a second rotational speed, wherein the x-ray detection assembly is mechanically decoupled from the first rotational apparatus and comprises at least one line detector configured to detect the narrow beam of x-ray photons, wherein the line detectors of the x-ray detection assembly operate in time-delay-integration mode; and
    c) a controller configured to perform at least:
        i) controlling the first rotational apparatus to rotate the x-ray generation assembly on the first trajectory at the first rotational speed;
        ii) controlling the second rotational apparatus to rotate the x-ray detection assembly on the second trajectory at the second rotational speed, around a target; and
        iii) controlling the speed and phase of rotation of the rotational collimator and the speed and phase of rotation of the x-ray detection assembly such that primary x-ray photons within the narrow beam of x-ray photons become incident upon the at least one line detector;
        wherein the second rotational speed is at least 10 times higher than the first rotational speed, wherein the first trajectory and the second trajectory are non-coplanar, wherein the first trajectory comprises less than 360 degrees rotation, and wherein the secondary trajectory comprises more than 360 degrees rotation.

2. The plural-plane narrow-beam CT system of claim 1, wherein the first trajectory varies both positively and negatively upon an axis perpendicular to the cross-sectional two-dimensional plane of rotation of the first rotational robotic.

3. The plural-plane narrow-beam CT system of claim 1, wherein the system does not comprise a gantry mechanically connecting the first rotational apparatus and the second rotational apparatus.

4. The plural-plane narrow-beam CT system of claim 1, wherein each line detector has a height at least an order of magnitude larger than its width.

5. The plural-plane narrow-beam CT system of claim 1, wherein the first rotational apparatus comprises a platform suspended from a vertically superior railing by which travel of x-ray generation assembly along the first trajectory is enacted.

6. The plural-plane narrow-beam CT system of claim 1, wherein the first rotational apparatus comprises a robotically controlled supporting platform by which travel of x-ray generation assembly along the first trajectory is enacted.

7. The plural-plane narrow-beam CT system of claim 1, wherein the second trajectory has a smaller average radius than the first trajectory.

8. The plural-plane narrow-beam CT system of claim 1, wherein the rotational collimator is configured to rotate about an axis of rotation on the first trajectory and perpendicular to the first trajectory.

9. The plural-plane narrow-beam CT system of claim 1, wherein the first trajectory comprises a non-linear ovoid plane.

10. The plural-plane narrow-beam CT system of claim 1, wherein the beam of x-ray photons incident on the x-ray detector comprises, in total, less than 10% scattered photons.

11. A plural-plane narrow-beam computed tomography (CT) system comprising:
    a) a first x-ray generation assembly affixed to a first rotational apparatus configured to rotate on a first trajectory at a first rotational speed;
    b) a second x-ray generation assembly affixed to a second rotational apparatus configured to rotate on a second trajectory at a second rotational speed;
        wherein each x-ray generation assembly comprises an x-ray tube and a rotational collimator, and wherein each x-ray generation assembly is configured to generate a narrow collimated beam of x-ray photons;
    c) an x-ray detection assembly affixed to a third rotational apparatus configured to rotate on a third trajectory at a third rotational speed, wherein the x-ray detection assembly is mechanically decoupled from the first and second rotational apparatuses and comprises at least one line detector configured to detect the narrow beams of x-ray photons; and
    d) a controller configured to perform at least:
        i) controlling the first rotational apparatus to rotate the first x-ray generation assembly on the first trajectory at the first rotational speed;
        ii) controlling the second rotational apparatus to rotate the second x-ray generation assembly on the second trajectory at the second rotational speed;
        iii) controlling the third rotational apparatus to rotate the x-ray detection assembly on the third trajectory at the third rotational speed, around a target; and
        iv) controlling the speed and phase of rotation of the rotational collimator of the first and second x-ray generation assemblies and the speed and phase of rotation of the x-ray detection assembly such that primary x-ray photons of the narrow beams generated by the first and second x-ray generation assemblies become incident upon the at least one line detector;

wherein the first trajectory comprises a rotation of at least 90 degrees plus one-half fan-angle, wherein the second trajectory comprises a rotation of at least 90 degrees plus one-half fan-angle, and wherein the third trajectory comprises more than 360 degrees rotation.

12. The plural-plane narrow-beam CT system of claim 11, wherein the first trajectory and the second trajectory are non-equivalent.

13. The plural-plane narrow-beam CT system of claim 11, wherein the first and second rotational apparatuses comprise independent platforms suspended from independent vertically superior railings.

14. The plural-plane narrow-beam CT system of claim 11, wherein the first and second rotational apparatuses are mounted upon independent robotic platforms.

15. The plural-plane narrow-beam CT system of claim 11, wherein the system does not comprise a gantry mechanically connecting the first rotational apparatus and the third rotational apparatus or the second rotational apparatus and the third rotational apparatus.

16. The plural-plane narrow-beam CT system of claim 11, wherein each line detector has a height at least an order of magnitude larger than its width.

17. The plural-plane narrow-beam CT system of claim 11, wherein the second trajectory has a smaller average radius than the first trajectory.

18. The plural-plane narrow-beam CT system of claim 11, wherein the beams of x-ray photons incident on the x-ray detector comprises, in total, less than 10% scattered photons.

19. A method of performing computed tomography (CT) to image a target, the method comprising:
   a) generating, by an x-ray generation assembly, a collimated narrow beam of x-ray photons having a fan angle of less than 5.8 degrees, the x-ray generation assembly affixed to a first rotational apparatus configured to rotate on a first trajectory at a first rotational speed, the x-ray generation assembly comprising at least one x-ray tube and a rotational collimator associated with each x-ray tube;
   b) detecting, by an x-ray detection assembly, the narrow beam of x-ray photons, the x-ray detection assembly affixed to a second rotational apparatus configured to rotate on a second trajectory at a second rotational speed, wherein the x-ray detection assembly is mechanically decoupled from the first rotational apparatus and comprises at least one line detector, and wherein the at least one line detector operates in time-delay-integration mode; and
   c) performing, by a controller unit, operations comprising:
      i) controlling the first rotational apparatus to rotate the x-ray generation assembly on the first trajectory at the first rotational speed;
      ii) controlling the second rotational apparatus to rotate the x-ray detection assembly on the second trajectory at the second rotational speed, around the target; and
      iii) controlling the speed and phase of rotation of the rotational collimator and the speed and phase of rotation of the x-ray detection assembly such that primary x-ray photons within the narrow beam of x-ray photons become incident upon the at least one line detector;

wherein the second rotational speed is at least 10 times higher than the first rotational speed, wherein the first trajectory and the second trajectory are non-coplanar, wherein the first trajectory comprises less than 360 degrees rotation, and wherein the secondary trajectory comprises more than 360 degrees rotation.

20. The method of claim 19, wherein a charge hand-off speed of the time-delay-integration mode of the at least one line detector is equal to the tangential speed of the detection assembly as it rotates on the second trajectory.

21. The method of claim 19, wherein the first trajectory varies both positively and negatively upon an axis perpendicular to the cross-sectional two-dimensional plane of rotation of the first rotational robotic.

22. The method of claim 19, wherein each line detector has a height at least an order of magnitude larger than its width.

23. The method of claim 19, wherein the first rotational apparatus comprises a platform suspended from a vertically superior railing by which travel of x-ray generation assembly along the first trajectory is enacted.

24. The method of claim 19, wherein the first rotational apparatus comprises a robotically controlled supporting platform by which travel of x-ray generation assembly along the first trajectory is enacted.

25. The method of claim 19, wherein the second trajectory has a smaller average radius than the first trajectory.

26. The method of claim 19, wherein the first trajectory comprises a non-linear ovoid plane.

27. The method of claim 19, wherein the beam of x-ray photons incident on the x-ray detector comprises, in total, less than 10% scattered photons.

28. A method of performing computed tomography (CT) to image a target, the method comprising:
   a) generating, by a first x-ray generation assembly, a collimated narrow beam of x-ray photons, the first x-ray generation assembly affixed to a first rotational apparatus configured to rotate on a first trajectory at a first rotational speed and comprising an x-ray tube and a rotational collimator;
   b) generating, by a second x-ray generation assembly, a collimated narrow beam of x-ray photons, the second x-ray generation assembly affixed to a second rotational apparatus configured to rotate on a second trajectory at a second rotational speed and comprising an x-ray tube and a rotational collimator;
   c) detecting, by an x-ray detection assembly, the narrow beams of x-ray photons, the x-ray detection assembly affixed to a third rotational apparatus configured to rotate on a third trajectory at a third rotational speed, wherein the x-ray detection assembly is mechanically decoupled from the first and second rotational apparatuses and comprises at least one line detector; and
   d) performing, by a controller unit, operations comprising:
      i) controlling the first rotational apparatus to rotate the first x-ray generation assembly on the first trajectory at the first rotational speed;
      ii) controlling the second rotational apparatus to rotate the second x-ray generation assembly on the second trajectory at the second rotational speed;
      iii) controlling the third rotational apparatus to rotate the x-ray detection assembly on the third trajectory at the third rotational speed, around the target; and
      iv) controlling the speed and phase of rotation of the rotational collimator of the first and second x-ray generation assemblies and the speed and phase of rotation of the x-ray detection assembly such that primary x-ray photons of the narrow beams generated by the first and second x-ray generation assemblies become incident upon the at least one line detector;

wherein the first trajectory comprises a rotation of at least 90 degrees plus one-half fan-angle, wherein the second trajectory comprises a rotation of at least 90 degrees plus one-half fan-angle, and wherein the third trajectory comprises more than 360 degrees rotation.

29. The method of claim 28, wherein each line detector has a height at least an order of magnitude larger than its width.

30. The method of claim 28, wherein the beams of x-ray photons incident on the x-ray detector comprises, in total, less than 10% scattered photons.

* * * * *